(12) United States Patent
Olcese

(10) Patent No.: US 8,992,589 B2
(45) Date of Patent: Mar. 31, 2015

(54) USING LIGHT TO REGULATE UTERINE CONTRACTIONS

(71) Applicant: The Florida State University Research Foundation, Inc., Tallahassee, FL (US)

(72) Inventor: James Olcese, Tallahassee, FL (US)

(73) Assignee: The Florida State University Research Foundation, Inc., Tallahassee, FL (US)

( * ) Notice: Subject to any disclaimer, the term of this patent is extended or adjusted under 35 U.S.C. 154(b) by 0 days.

(21) Appl. No.: 13/938,485

(22) Filed: Jul. 10, 2013

(65) Prior Publication Data

US 2014/0094877 A1 Apr. 3, 2014

Related U.S. Application Data

(63) Continuation-in-part of application No. 13/896,507, filed on May 17, 2013, and a continuation-in-part of application No. 12/745,819, filed as application No. PCT/US2008/013317 on Dec. 3, 2008, now Pat. No. 8,445,436.

(60) Provisional application No. 60/991,866, filed on Dec. 3, 2007, provisional application No. 61/740,524, filed on Dec. 21, 2012, provisional application No. 61/669,748, filed on Jul. 10, 2012.

(51) Int. Cl.
*A61N 5/06* (2006.01)
*A61K 31/4045* (2006.01)
*A61K 38/11* (2006.01)

(52) U.S. Cl.
CPC .............. *A61N 5/0618* (2013.01); *A61N 5/06* (2013.01); *A61N 5/0603* (2013.01); *G01N 2800/368* (2013.01); *A61K 31/4045* (2013.01); *A61K 38/11* (2013.01)
USPC .......................................... 607/88; 514/12.1

(58) Field of Classification Search
None
See application file for complete search history.

(56) References Cited

U.S. PATENT DOCUMENTS

| | | | |
|---|---|---|---|
| 7,899,527 B2 | 3/2011 | Yun et al. | |
| 2002/0012677 A1 | 1/2002 | Levine et al. | |
| 2004/0038855 A1 | 2/2004 | Salon et al. | |
| 2006/0204532 A1 | 9/2006 | John | |
| 2012/0296400 A1 | 11/2012 | Bierman et al. | |

OTHER PUBLICATIONS

Ducsay and Yellon, Biology of Reproduction, 1991; 44: 967-974.*
Olcese and Beesley, Fertil Steril., 2014; 102: 329-335.*
Olcese et al., Melatonin and the Circadian Timing of Human Parturition, Reproductive Sciences 00(0), 2012.
Figueiro et al, Implications of controlled short-wavelength light exposure for sleep in older adults, BMC Research Notes, 2011, 4:334.
Figueiro et al., A personal light-treatment device for possibly improving sleep quality in the elderly: Dynamics of nocturnal melatonin suppression at two exposure levels, Chronobiol Int., May 2009, 26(4): 726-739.
Figueiro et al., Preliminary evidence that light through the eyelids can suppress melatonin and phase shift dim light melatonin onset, BMC Research Notes, 2012, 5:221.
Figueiro et al., A train of blue light pulses delivered through closed eyelids suppresses melatonin and phase shifts the human circadian system, Nature and Science of Sleep, 2013, 5, 133-141.
Schlabritz-Loutesvitch et al., The Human Myometrium as a Target for Melatonin, The Journal of Clinical Endocrinology & Metabolism, 88(2): 908-913, 2003.
Sarna et al., Intravenous Oxytocin in Patients Undergoing Elective Cesarean Section, Anesth Analg, 1997, 84:753-756.
Roizen et al., Oxytocin in the Circadian Timing of Birth, Plos one, Sep. 2007, Issue 9.
Simhan et al., Prevention of Preterm Delivery, N Engl J. Med., 2007; 357, 477-487.
Engstrom et al., Effect of Oxytocin Receptor and B2-Adrenoceptor Blockade on Myometrial Oxytocin Receptors in Parturient Rats, Biology of Reproduction, 60, 322-329, 1999.
Shors et al., Testosterone in utero at at birth dictates how stressful experience will affect learning in adulthood, PNAS, Oct. 15, 2002, vol. 99, No. 21, 13955-13960.
Sharkey et al., Melatonin Synergizes with Oxytocin to Enhance Contractility of Human Myometrial Smooth Muscle Cells, J Clin endocrinol Metab, Feb. 2009, 94(2) 421-427.
Martensson et al., Melatonin together with noradrenaline augments contractions of human myometrium, European Journal of Pharmacology 316 (1996), 273-275.
Khalifal, Tocolytic Effect of Melatonin: Possible Modification of Uterine Response to Certain Drugs by Pretreatment With Melatonin in Non-Pregnant Rats, Bull Enc. Pharm, Cairo Univ. vol. 35, No. 3, 1997.
Sharkey et al., Transcriptional Inhibition of Oxytocin Receptor Expression in Human Myometrial Cells by Melatonin Involves Protein Kinase C Signaling, The Journal of Clinical Endocrinology & Metabolism, 92(10), 4015-4019, 2007.
Juszczak et al., Role of Tachykinin Receptors and Melatonin in Oxytocin Secretion From Isolated Rat Hypothalmo-neurohypophysial System, Journal of Physiology and Pharmacology, 2004, 55, 4, 739-749.
Svoren, Sexual development in a 21 month-old boy caused by testosterone contamination of a topical hydrocortisone cream, J Pediatr Endocrinol Metab. May 2005, 18 (5): 507-510.
Medline Plus, Testosterone Topical, http:/www.hlm.nih.gov/medlineplus/druginfo/meds/a605020.html, downloaded Mar. 21, 2013.
LA Times, Testosterone cream: bad for babies FDA warns, LA Times, May 7, 2009.
Internatioinal Search Report for PCT/US/2008/013317.
Sharkey, Melatonin Regulation of the Oxytocin System in the Pregnant Human Uterus, (2009), Electronic Theses, Treatises and Dissertations, Paper 1791, Nov. 4, 2009.

* cited by examiner

*Primary Examiner* — Christina Borgeest
(74) *Attorney, Agent, or Firm* — Allen, Dyer, Doppelt, Milbrath & Gilchrist, P.A.

(57) ABSTRACT

Methods of regulating uterine contractions using light are described. An exemplary method of regulating uterine contractions comprises suppressing a nocturnal endogenous melatonin level of a pregnant female experiencing uterine contractions by exposing the pregnant female during nighttime to a light source emitting visible light.

11 Claims, 3 Drawing Sheets

USING LIGHT TO REGULATE UTERINE CONTRACTIONS

CROSS-REFERENCE TO RELATED APPLICATIONS

This is a continuation-in-part of application Ser. No. 13/896,507, filed May 17, 2013, which is a continuation of application Ser. No. 12/745,819, filed Jul. 21, 2010, now U.S. Pat. No. 8,445,436, which is the national stage entry of Application No. PCT/US08/13317, filed Dec. 3, 2008, which claimed priority to provisional application Ser. No. 60/991,886, filed Dec. 3, 2007. This also claims priority to provisional application Ser. No. 61/740,524, filed Dec. 21, 2012, and provisional application Ser. No. 61/669,748, filed Jul. 10, 2012.

FIELD OF THE INVENTION

The invention relates to the field of pregnancy and, more particularly, to methods of regulating uterine contractions.

BACKGROUND

Parturition is a physiological process that occurs when pregnant females are in labor. It is characterized by increasingly frequent uterine contractions and cervical effacement, which ultimately leads to delivery of offspring. Parturition is a complex physiological and molecular biological process that has evolved differently in different species due to each species' unique environmental and temporal niches. Most mammals have adapted to selective pressures, such as the availability of food and prevalence of predators, by developing either a diurnal or nocturnal activity phase. Pregnant females have adapted to deliver their offspring in their den or home camp rather than in the field, which enhances their safety, security, and birth success.

The selective advantage for entering parturition during the daytime or nighttime phases is reflected in the differential timing of this event among many species of nocturnal rodents and diurnal mammals, such as sheep and primates. Rats, for example, enter parturition predominantly during the day time, even when the light-dark cycles are reversed. [1-3] Similarly, golden hamsters develop strong uterine contractions and deliver their young during daytime hours. [4] Humans, on the other hand, tend to enter labor during the late nighttime and early morning hours [5-9] with parturition typically following 12 to 24 hours thereafter, at least in nulliparous women. [7] The frequency of uterine contractions in preterm women at risk for spontaneous premature delivery increases significantly at night. [10]

In nonhuman primates, the late-term myometrial contractions and the sensitivity of the uterus to the contractile effects of oxytocin have been shown to be the highest early in the night phase. [11-13] In addition, the phasing of nocturnal parturition in nonhuman primates has been shown to also be shifted by reversal of the light/dark cycles [14], pointing to a light-sensitive clock mechanism underlying parturition. Since both humans and nonhuman primates show nocturnally peaking uterine contractions in late-term pregnancy [15-17], the intriguing question arises—what are the circadian signals that drive nocturnal uterine activity in late term human pregnancy?

Maintenance of appropriate circadian phase in peripheral tissues requires zeitgebers (entraining cues) that are coupled with the central circadian oscillator in the brain's suprachiasmatic nuclei (SCN) via neural pathways, rhythmic endocrine, and/or metabolic signals. For many peripheral clocks, such as the liver, heart, pancreas, and so on, autonomically driven neuroendocrine output cues such as melatonin and glucocorticoids are considered to play a key role. [18] Evidence continues to accumulate showing that these two hormones have significant effects on the endogenous circadian clockwork in a variety of peripheral tissues. [19-24]

SUMMARY

Melatonin plays a role in stimulating uterine contractions. Exposing pregnant females to light during nocturnal hours decreases their endogenous melatonin levels, which regulates nocturnal uterine contractions. The various method aspects of the invention take advantage of this phenomenon.

In a first method aspect of the invention, a method of regulating uterine contractions comprises suppressing a nocturnal endogenous melatonin level of a pregnant female experiencing uterine contractions by exposing the pregnant female during nighttime to a light source emitting visible light.

In a second method aspect of the invention, a method of regulating uterine contractions in a pregnant female comprises selecting a pregnant female experiencing uterine contractions, directing light from a light source emitting visible light onto the pregnant females eyes at night, the intensity of the visible light being sufficient to suppress the pregnant female's endogenous melatonin level.

In a third method aspect of the invention, a method of regulating nocturnal uterine contractions during preterm labor comprises exposing a pregnant female experiencing preterm labor to a light source at night, the light source emitting visible light effective to suppress the pregnant female's endogenous melatonin level.

These and other objects, aspects, and advantages of the invention will be better appreciated in view of the following detailed description of preferred embodiments and the accompanying drawings.

DETAILED DESCRIPTION OF PREFERRED EMBODIMENTS

Figure 1:
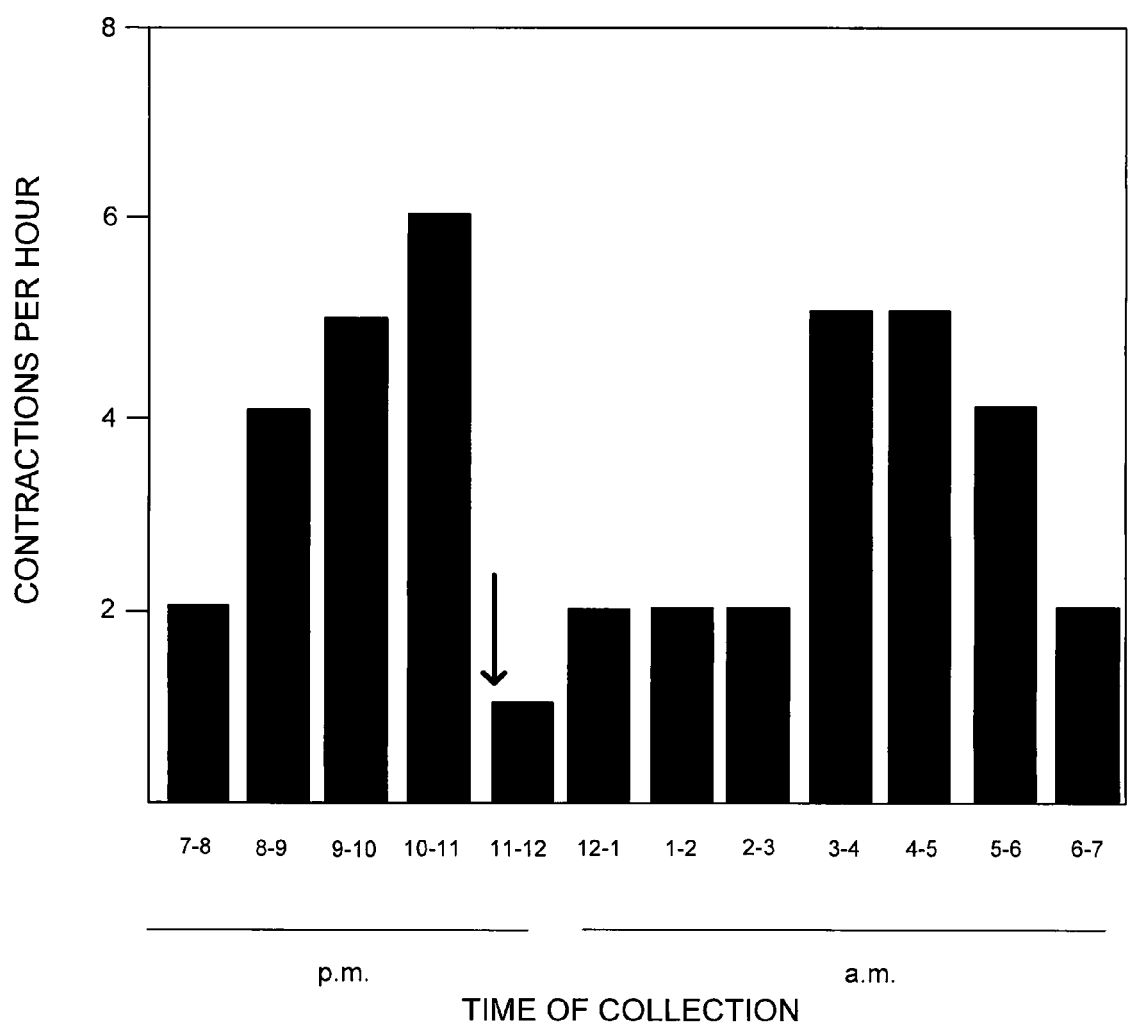
FIG. 1 is a bar graph showing the number of contractions per hour a pregnant volunteer experienced overnight and how the number changed when a lamp was turned on for about one hour.

In the Summary above and in the Detailed Description of Preferred Embodiments, reference is made to particular features (including method steps) of the invention. Where a particular feature is disclosed in the context of a particular aspect or embodiment of the invention, that feature can also be used, to the extent possible, in combination with and/or in the context of other particular aspects and embodiments of the invention, and in the invention generally.

The term "comprises" is used herein to mean that other ingredients, features, steps, etc. are optionally present. When reference is made herein to a method comprising two or more defined steps, the steps can be carried in any order or simultaneously (except where the context excludes that possibility), and the method can include one or more steps which are carried out before any of the defined steps, between two of the defined steps, or after all of the defined steps (except where the context excludes that possibility).

In this section, the invention will be described more fully with reference to certain preferred embodiments. This invention may, however, be embodied in many different forms and should not be construed as limited to the embodiments set forth herein. Rather, these embodiments are provided so that this disclosure will convey preferred embodiments of the invention to those skilled in the art.

As discussed above, the various method aspects of the invention are directed to regulating uterine contractions by exposing pregnant females to light. The term "regulating," in this context means reducing the number of uterine contractions over a given time period, reducing the intensity of the uterine contractions, and or preventing uterine contractions from occurring when they might otherwise occur in the absence of light. These methods are useful, for example, to prolong pregnancy, prevent preterm birth, or, if preterm birth is inevitable, to delay the preterm birth.

The endogenous melatonin level of a typical person rises gradually from about 9:00 p.m. to a maximum at about 2:00 a.m. After about 2:00 a.m., the endogenous melatonin level gradually decreases until morning and remains very low throughout the day. The cycle then repeats itself the following night. Because the endogenous melatonin level reaches its peak at night, this is the time period during which melatonin stimulates the most contractions. By exposing a pregnant female to a light source with sufficient intensity to suppress the endogenous melatonin level, uterine contractions are suppressed. In this context "suppressing" the endogenous melatonin level refers to either reducing the endogenous melatonin level from normal or preventing the endogenous melatonin level from rising as it normally would at night.

A method of regulating uterine contractions, according to a first method aspect of the invention, involves suppressing the nocturnal endogenous melatonin level of a pregnant female experiencing uterine contractions by exposing the pregnant female during nighttime to a light source emitting visible light.

A method of regulating uterine contractions in a pregnant female, according to a second method aspect of the invention, involves selecting a pregnant female experiencing uterine contractions and directing light from a light source emitting visible light onto the pregnant female's eyes at night. The intensity of the visible light is sufficient to suppress the pregnant female's endogenous melatonin level.

A method of regulating nocturnal uterine contractions during preterm labor, according to a third method aspect of the invention, involves exposing a pregnant female experiencing preterm labor to a light source at night, where the light source emits visible light effective to suppress the pregnant female's endogenous melatonin level.

The light source must be of sufficient intensity and color to be able to suppress the endogenous melatonin level. In the experiment described in the Example, the light source was a full spectrum 10,000 lux phototherapy lamp positioned about 1 meter from the pregnant female's eyes. Although this yielded good results, other light sources are suitable for use in the methods. A suitable intensity range for the light source is about 1,000 to about 10,000 lux.

The light source spectrum may be tuned to optimize the amount of melatonin suppression. One preferred light source predominantly emits blue light. Blue light in the wavelength range of about 450 to about 500 nm is particularly preferred.

The pregnant female is exposed to the light during typical nocturnal or nighttime hours, preferably between about 9 p.m. to about 6 a.m. The pregnant female may be exposed to the light source continuously throughout the night or in smaller time increments during the night.

In some embodiments, the light source is a headset or set of goggles. The headset includes a body attached to the wearer's head for supporting a first light over the pregnant female's left eye and a second light over the pregnant female's right eye.

Optionally, the light source is adapted to emit light in discrete on/off cycles or pulses. The duration of the pulses and the separation between successive pulses is adjusted to obtain the desired amount of endogenous melatonin suppression.

EXAMPLE

This section describes clinical experiments performed on actual pregnant female human patients. It is not intended to limit the scope of the invention in any way Pregnant female human volunteers at >38 weeks of gestation were studied to determine whether exposing them to visible light would suppress their uterine contractions during the nighttime hours and whether the suppression of uterine contractions that might result from light exposure is correlated with a decrease in their endogenous melatonin levels. In the experiments, women were studied by continuously monitoring their uterine contractions from 7:00 p.m. until 7:00 a.m. under dim light. At 11:00 p.m., each woman was exposed to a 10,000 lux, full spectrum phototherapy lamp positioned about 1 meter from the woman's eyes. After about 1 hour, the lamp was turned off. The contractions were recorded by a registered obstetric nurse. The study was performed in a hospital after receiving approval from the appropriate institutional review boards.

Figure 2:
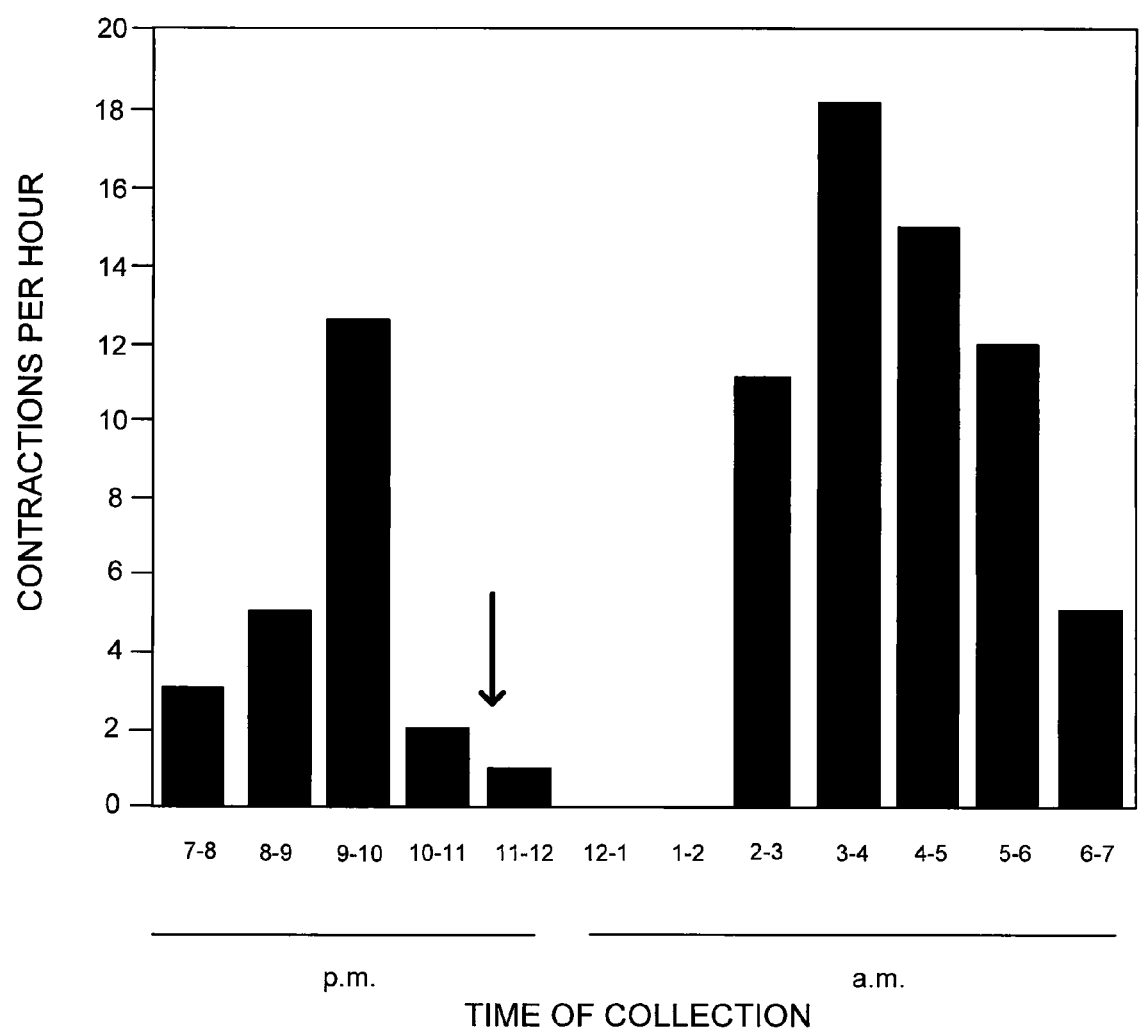
FIG. 2 is a bar graph showing the number of contractions per hour another pregnant volunteer experienced overnight and how the number changed when a lamp was turned on for about one hour.
Figure 3:
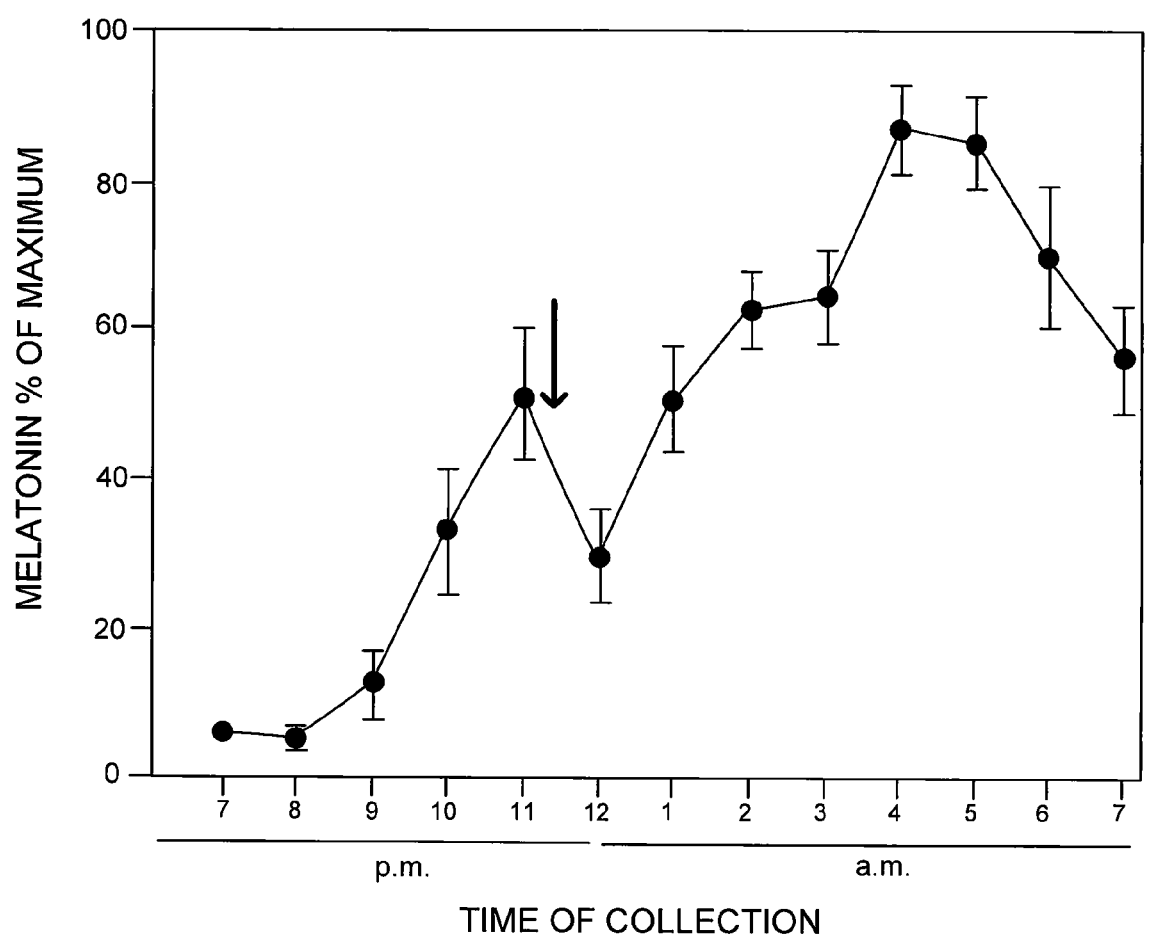
FIG. 3 is a line graph showing composite results of the melatonin level of five pregnant volunteers when a lamp was turned on for about an hour.

The results of these experiments are shown in FIGS. 1-3. FIGS. 1 and 2 show the number of contractions two different women experienced per hour. FIG. 3 shows the composite results of the melatonin levels of the women studied. The arrow in each graph represents the time at which the lamp was turned on.

The results show that, when the lamp was turned on at about 11:00 p.m., the number of contractions experienced by the women per hour decreased substantially. When the lamp was turned off after about 1 hour, the number of contractions the women experienced per hour gradually rose before eventually decreasing during the early morning hours. FIG. 3 shows that the women's endogenous melatonin levels gradually rose until 11:00 p.m. when the lamp was turned on and dropped by about 45% during the ~1 hr that the lamp was activated. Once the lamp was turned off, their melatonin levels gradually rose throughout the night before decreasing during the early morning hours. When combined, the results indicate that there is indeed a direct correlation between melatonin levels and uterine contractions.

The results reveal that regular nocturnal contractions are suppressed by bright light exposure under these conditions. This finding supports the proposition that melatonin is a key zeitgeber, regulating the onset of human labor and parturition and that light can be used to regulate melatonin levels and, thereby, regulate uterine contractions.

The invention has been described above with reference to preferred embodiments. Unless otherwise defined, all technical and scientific terms used herein are intended to have the same meaning as commonly understood in the art to which this invention pertains and at the time of its filing. Although various methods and materials similar or equivalent to those described herein can be used in the practice or testing of the present invention, suitable methods and materials are described. However, the skilled should understand that the methods and materials used and described are examples and may not be the only ones suitable for use in the invention. Various modifications of the embodiments described here can be made without departing from the spirit and scope of the invention as described above and as defined in the appended claims.

REFERENCES

1. Plaut S M, Grota L J, Ader R, Graham C W. Effects of handling and the light-dark cycle on time of parturition in the rat. Lab Anim Care. 1970; 20(3):447-453.
2. Boer K, Lincoln D W, Swaab D F. Effects of electrical stimulation of the neurohypophysis on labour in the rat. J Endocrinol. 1975; 65(2):163-176.
3. Lincoln D W, Porter D G. Timing of the photoperiod and the hour of birth in rats. Nature. 1976; 260(5554):780-781.
4. Siegel H I, Greenwald G S. Prepartum onset of maternal behavior in hamsters and the effects of estrogen and progesterone. Horm Behav. 1975; 6(3):237-245.
5. Glattre E, Bjerkedal T. The 24-hour rhythmicity of birth: a population study. Acta Obstet Gynecol Scand. 1983; 62:31-36.
6. Cooperstock M, England J E, Wolfe R A. Circadian incidence of labor onset hour in preterm birth and chorioamnionitis. Obstet Gynecol. 1987; 70(6):852-855.
7. Cagnacci A, Soldani R, Melis G B, Volpe A. Diurnal rhythms of labor and delivery in women: modulation by parity and seasons. Am J Obstet Gynecol. 1998; 178(1 pt 1):140-145.
8. Lindow S W, Jha R R, Thompson J W. 24-hour rhythm to the onset of preterm labour. Br J Obstet Gynecol. 2000; 107(9): 1145-1148.
9. Vatish M, Steer P J, Blanks A M, Hon M, Thornton S. Diurnal variation is lost in preterm deliveries before 28 weeks of gestation. Br J Obstet Gynecol. 2010; 117(6): 765-767.
10. Iams J D, Newman R B, Thom E A, et al. Frequency of uterine contractions and the risk of spontaneous preterm delivery. N Engl J Med. 2002; 346(4):250-255.
11. Harbert G M Jr. Biorhythms of the pregnant uterus (Macaca mulatta). Am J Obstet Gynecol. 1977; 129(4): 401-408.
12. Morgan M A, Silavin S L, Wentworth R A, et al. Different patterns of myometrial activity and 24-h rhythms in myometrial contractility in the gravid baboon during the second half of pregnancy. Biol Reprod. 1992; 46(6):1158-1164.
13. Honnebier M B O M, Myers T, Figueroa J P, Nathanielsz P W. Variations in myometrial response to intravenous oxytocin administration at different times of the day in the pregnant rhesus monkey. Endocrinology. 1989; 125(3): 1498-1503.
14. Ducsay C A, Yellon S M. Photoperiod regulation of uterine activity and melatonin rhythms in the pregnant rhesus macaque. Biol Reprod. 1991; 44(6):967-974.
15. Main D M, Grisso J A, Wold T, Snyder E S, Holmes J, Chiu G. Extended longitudinal study of uterine activity among low-risk women. Am J Obstet Gynecol. 1991; 165(5 pt 1):1317-1322.
16. Zahn V, Hattensperger W. Circadian rhythm of pregnancy contractions. Z Geburtshilfe Perinatol. 1993; 197(1):1-10.
17. Farber D M, Giussani D A, Jenkins S L, et al. Timing of the switch from myometrial contractures to contractions in late-gestation pregnant rhesus monkeys as recorded by myometrial electromyogram during spontaneous term and androstenedione-induced labor. Biol Reprod. 1997; 56(2): 557-562.
18. Prasai M J, Pernicova I, Grant P J, Scott E M. An endocrinologist's guide to the clock. J Clin Endocrinol Metab. 2011; 96(4):913-922.
19. Messager S, Hazlerigg D G, Mercer J G, Morgan P J. Photoperiod differentially regulates the expression of Per1 and ICER in the pars tuberalis and the suprachiasmatic nucleus of the Siberian hamster. Eur J Neurosci. 2000; 12(8):2865-2870.
20. von Gall C, Garabette M L, Kell C A, et al. Rhythmic gene expression in pituitary depends on heterologous sensitization by the neurohormone melatonin. Nat Neurosci. 2002; 5(3):234-238.
21. Imbesi M, Dirim D A, Yildiz S, et al. The melatonin receptor MT1 is required for the differential regulatory actions of melatonin on neuronal clock gene expression in striatal neurons in vitro. J Pineal Res. 2009; 46(1):87-94.
22. Balsalobre A. Clock genes in mammalian peripheral tissues. Cell Tissue Res. 2002; 309(1):193-199.
23. Dickmeis T. Glucocorticoids and the circadian clock. J Endocrinol. 2009; 200(1):3-22.
24. Kiessling S, Eichele G, Oster H. Adrenal glucocorticoids have a key role in circadian resynchronization in a mouse model of jet lag. J Clin Invest. 2010; 120(7):2600-2609.

That which is claimed is:

1. A method of reducing uterine contractions occurring at night in a late-term pregnant human female, the method comprising suppressing the regular nocturnal endogenous melatonin secretions of said late-term pregnant human female experiencing uterine contractions by directing into the eyes of the pregnant human female during the night blue light from a light source having a wavelength of about 450 to 500 nm and an intensity of about 1,000 to 10,000 lux.

2. The method of claim 1, wherein the light source intensity is about 10,000 lux.

3. The method of claim 1, wherein the light source intensity is about 10,000 lux and the light source is positioned about 1 meter from the eyes.

4. The method of claim 1, wherein exposure to the light source occurs between 9 p.m. to 6 a.m.

5. A method of reducing uterine contractions occurring at night in a late-term pregnant human female, the method comprising suppressing the regular nocturnal endogenous melatonin secretions of said late-term pregnant human female experiencing uterine contractions by directing into the eyes of the pregnant human female intermittently during the night blue light pulses from a light source having a wavelength of about 450 to 500 nm and of an intensity of about 1,000 to 10,000 lux.

6. The method of claim 5, wherein the intensity is about 10,000 lux.

7. The method of claim 5, wherein the intensity is about 10,000 lux and the light source is positioned about 1 meter from the eyes.

8. The method of claim 5, wherein exposure to the light source occurs between 9 p.m. to 6 a.m.

9. A method of reducing nocturnal uterine contractions in a late-term pregnant human female during preterm labor, the method comprising suppressing the regular nocturnal endogenous melatonin secretions of said late-term pregnant human female experiencing uterine contractions by directing into the eyes of the pregnant human female intermittently during the night blue light pulses from a light source having a wavelength of about 450 to 500 nm and of an intensity of about 1,000 to 10,000 lux wherein the light source comprises a headset having a light source for each of the eyes.

10. The method of claim 9, wherein the light source intensity is about 10,000 lux.

11. The method of claim 9, wherein exposure to the light source occurs between 9 p.m. to 6 a.m.

\* \* \* \* \*